(12) United States Patent
Proctor Beauchamp et al.

(10) Patent No.: US 11,031,133 B2
(45) Date of Patent: Jun. 8, 2021

(54) ANALYSING TEXT-BASED MESSAGES SENT BETWEEN PATIENTS AND THERAPISTS

(71) Applicant: IESO Digital Health Limited, Cambridgeshire (GB)

(72) Inventors: Guy James Proctor Beauchamp, Cambridgeshire (GB); Ann Gail Hayes, Cambridgeshire (GB); Christine Howes, Cambridgeshire (GB); Rosemarie McCabe, Cambridgeshire (GB); Barnaby Adam Perks, Cambridgeshire (GB); Matthew Richard John Purver, Cambridgeshire (GB); Sarah Elisabeth Bateup, Cambridgeshire (GB)

(73) Assignee: IESO Digital Health Limited, Cambridgeshire (GB)

( * ) Notice: Subject to any disclaimer, the term of this patent is extended or adjusted under 35 U.S.C. 154(b) by 981 days.

(21) Appl. No.: 15/524,756

(22) PCT Filed: Nov. 6, 2014

(86) PCT No.: PCT/GB2014/053311
§ 371 (c)(1),
(2) Date: May 5, 2017

(87) PCT Pub. No.: WO2016/071659
PCT Pub. Date: May 12, 2016

(65) Prior Publication Data
US 2017/0323065 A1 Nov. 9, 2017

(51) Int. Cl.
*G06N 3/08* (2006.01)
*G16H 50/20* (2018.01)
(Continued)

(52) U.S. Cl.
CPC ............ *G16H 50/20* (2018.01); *A61B 5/165* (2013.01); *G06F 19/00* (2013.01); *G06N 20/00* (2019.01)

(58) Field of Classification Search
CPC ................................. G16H 50/20; A61B 5/165
See application file for complete search history.

(56) References Cited

U.S. PATENT DOCUMENTS

| | | | |
|---|---|---|---|
| 2005/0228236 A1* | 10/2005 | Diederich | A61B 5/7267 600/300 |
| 2007/0166690 A1* | 7/2007 | Johnson | G09B 19/00 434/365 |

(Continued)

FOREIGN PATENT DOCUMENTS

WO 2016071659 A1 5/2016

OTHER PUBLICATIONS

Saggion, Horacio, et al. "NLP Resources for the Analysis of Patient/Therapist Interviews." Proceedings of the Seventh conference on International Language Resources and Evaluation (LREC'10). 2010. (Year: 2010).*

(Continued)

*Primary Examiner* — Hal Schnee
(74) *Attorney, Agent, or Firm* — Vorys, Sater, Seymour and Pease LLP

(57) ABSTRACT

A computer-implemented method comprising: obtaining text from text-based messages sent between a patient and a therapist providing psychological therapy; determining at least one feature of the text; and determining a characteristic of the patient and/or the therapist using the at least one feature.

27 Claims, 2 Drawing Sheets

(51) Int. Cl.
*G06N 20/00* (2019.01)
*G06F 19/00* (2018.01)
*A61B 5/16* (2006.01)

(56) References Cited

U.S. PATENT DOCUMENTS

| | | | |
|---|---|---|---|
| 2008/0133221 A1* | 6/2008 | Smith | G06F 40/258 |
| | | | 704/9 |
| 2012/0320145 A1 | 12/2012 | Kahn | |
| 2013/0018824 A1* | 1/2013 | Ghani | G06N 20/00 |
| | | | 706/12 |
| 2014/0046696 A1* | 2/2014 | Higgins | G16B 40/00 |
| | | | 705/3 |
| 2014/0136450 A1* | 5/2014 | Lee | G06N 7/005 |
| | | | 706/11 |
| 2016/0022193 A1* | 1/2016 | Rau | A61B 5/165 |
| | | | 600/301 |
| 2016/0098480 A1* | 4/2016 | Nowson | G06F 40/30 |
| | | | 707/738 |

OTHER PUBLICATIONS

Gil, Gonzalo Blázquez et al. "Combining machine learning techniques and natural language processing to infer emotions using Spanish Twitter corpus." International Conference on Practical Applications of Agents and Multi-Agent Systems. Springer, Berlin, Heidelberg, 2013. (Year: 2013).*

Poulin, Chris, et al. "Predicting the risk of suicide by analyzing the text of clinical notes." PloS one 9.1 (2014). (Year: 2014).*

Castonguay, Louis G., et al. "Predicting the Effect of Cognitive Therapy for Depression: A Study of Unique and Common Factors." Journal of Consulting and Clinical Psychology 64.3 (1996): 497-504. (Year: 1996).*

International Search Report received in corresponding PCT Application PCT/GB2014/053311, dated Jun. 24, 2015.

* cited by examiner

ANALYSING TEXT-BASED MESSAGES SENT BETWEEN PATIENTS AND THERAPISTS

FIELD

The present invention relates, amongst other things, to a method of analysing text-based messages sent between patients and therapists.

BACKGROUND

Computer-based systems for providing psychological therapy are being developed in which patients and therapists can communicate using text-based messages.

SUMMARY

According to a first aspect of the present invention, there is provided a (computer-implemented) method comprising:
 obtaining text from text-based messages sent between a patient and a therapist providing psychological therapy;
 determining at least one feature of the text; and
 determining a characteristic of the patient and/or the therapist using the at least one feature.

Thus, the method can provide an effective and efficient way of determining characteristics of patients and/or therapists by analysing the text-based messages sent therebetween. This can enable, for example, alerting of particular situations or scenarios of concern.

Optional features are specified in the dependent claims.

BRIEF DESCRIPTION OF THE DRAWINGS

Certain embodiments of the present invention will now be described, by way of example only, with reference to the accompanying drawings in which.

DETAILED DESCRIPTION OF THE CERTAIN EMBODIMENTS

System

Figure 1:
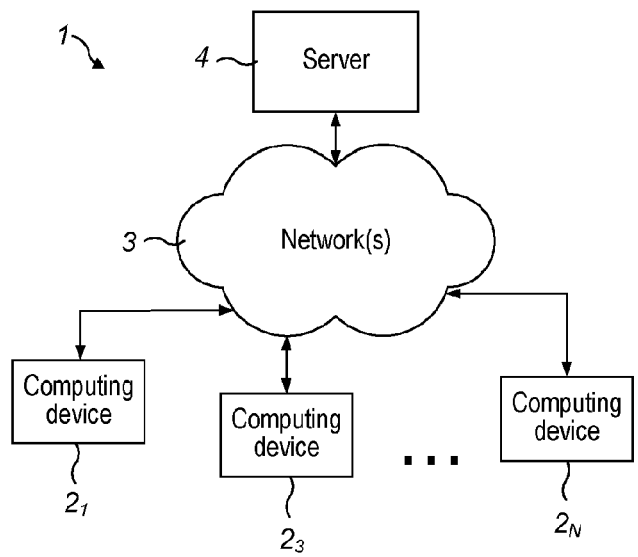
FIG. 1 illustrates a computer-based system for providing psychological therapy.

Referring to FIG. 1, a computer-based system 1 for providing psychological therapy will now be described. The system 1 includes a plurality of computing devices 2 connectable, via one or more networks 3, to a server 4.

The computing devices 2 may be of any type. The computing devices 2 are preferably configured to run a web browser software application. Users of the computing devices 2 include patients and therapists providing psychological therapy, e.g. cognitive behavioural therapy. Users of the computing device 2 may also include supervisors of the therapists.

The network system 3 preferably includes the Internet.

Figure 2:
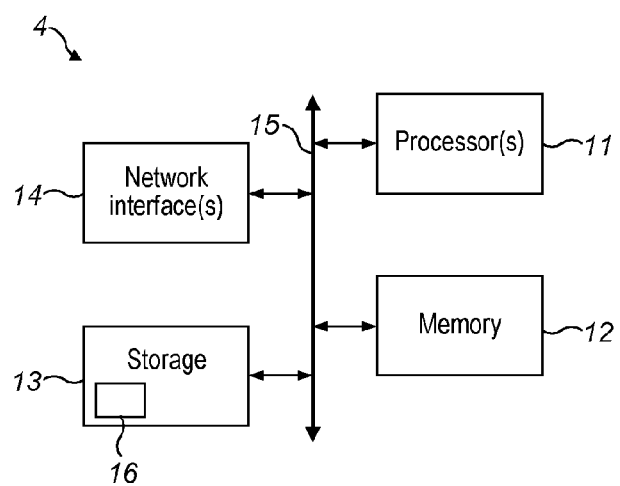
FIG. 2 illustrates a server included in the system of FIG. 1.

Referring to FIG. 2, the server 4 preferably includes one or more processors 11, volatile and non-volatile memory 12, 13, and one or more network interfaces 14, interconnected by a bus 15. The server 4 may include several units as illustrated in FIG. 2 interconnected via a network. The non-volatile memory 13 stores computer-readable instructions 16. When executed, the computer-readable instructions cause the server 4 to perform the functions described below.

The server 4 is configured to enable text-based messages to be sent between patients and therapists. At least some of the messages are preferably sent via an instant messaging system. This may be achieved in any suitable way. For example, the server 4 may provide a web interface to enable users to login and send messages. As will be described in more detail below, the server 4 is configured to analyse text obtained from these messages. The server 4 may comprise a specially configured module configured to perform this function. The server 4 may be configured to taken actions, e.g. provide alerts to therapists and/or supervisors, after analysing the text.

Method

Figure 3:
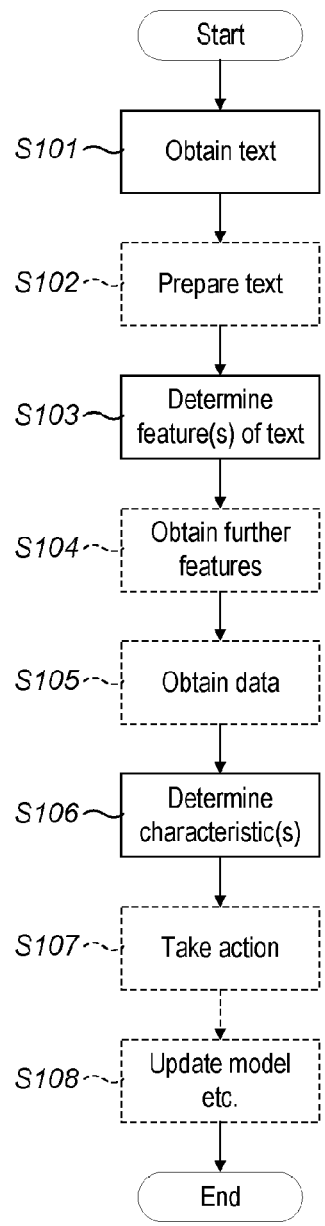
FIG. 3 illustrates a method that can be performed by the server of FIG. 2.

Referring to FIG. 3, a method that can be performed by the server 4 will now be described.

At a first step S101, the server 4 obtains text from text-based messages sent between a patient and a therapist.

The text is preferably obtained from messages sent by the patient and by the therapist. However, this need not be the case. The text is preferably obtained from messages corresponding to one session of therapy, e.g. a period during which instant messages are exchanged. However, the text may be obtained from messages corresponding to more or less than one session or from messages send at times other than during sessions. The text may be obtained from messages sent by more than one patient and/or more than one therapist.

The method preferably starts automatically, e.g. after detecting that a session of therapy has been completed.

At an optional second step S102, the server 4 prepares the text obtained at the first step S101. This preferably involves replacing words (or sequences of words) with alternatives, wherein each alternative can replace several different words (or sequences of words). For example, various misspellings or abbreviations can be replaced by corrected/full words. The step also preferably involves removing stop words, e.g. common words which do not contribute to the content such as 'the' and 'to'.

At a third step S103, the server 4 determines one or more features of the text obtained at the first step S101 and optionally prepared at the second step S102. The server 4 preferably determines several features of the text.

The features determined at the third step S103 may include one or more values describing a level to which the text relates to a topic. There are preferably several values, each of which describes (parameterises) a level to which the text relates to a different topic. The topics are preferably determined using a topic model and text obtained from other messages between patients and therapists.

Alternatively or additionally, the features may include one or more values describing an emotional state. For example, there may be a value describing positive/negative sentiment and a value describing anger. The values may describe a level or a variability of the emotional state. The values are preferably determined using a model obtained using supervised machine learning. The model is preferably obtained using training data comprising text from another source. However, this need not be the case.

Alternatively or additionally, the features may include one or more values describing or relating to a frequency of a word or sequence of words in the text. There are preferably several values, each of which describes the frequency of a different word/sequence of words. The words/sequences of words preferably correspond to a set of frequently used words/sequences of words in text obtained from other messages between patients and therapists (not including stop words).

The server 4 may determine other type of features, e.g. features relating to level of repetition, reformulation or correction, complexity of syntax or vocabulary, level of similarity between therapist and patient, (sequences of) part-of-speech tags, (sub-parts of) syntactic structures, (sequences of) dialogue act tags or other indicators of pragmatic function, etc.

The features may be stored for later use.

At an optional fourth step S104, the server 4 obtains one or more, and preferably several, further features. The further features preferably include features ('previous features') of text obtained from messages sent during one or more previous sessions of the patient. The previous features are preferably obtained from data stored at the server 4.

The further features may include features that are a function of one or more other features. For example, a feature may correspond to a difference between a feature ('a current feature') obtained at the third step S103 and a previous feature.

At an optional fifth step S105, the server 4 obtains data relating to the patient (e.g. demographic data, questionnaire scores), the therapist (e.g. an identity thereof) and/or the communications therebetween (e.g. session number, number of words in the text, etc.).

The server 4 is preferably configured to provide a web interface to enable a patient to complete one or more questionnaires and to determine a score therefrom. The questionnaires may include, for example, questionnaires relating to depression and anxiety. This is preferably performed for each session. However, this need not be the case. For example, the analysis described herein may render this unnecessary.

At a sixth step S106, the server 4 determines a characteristic of the patient and/or the therapist using the features obtained at the third step S103, the further features optionally obtained at the fourth step S104 and the data optionally obtained at the fifth step S105.

In some examples, this is performed using a model obtained using supervised machine learning. As will be explained in more detail below, the model is preferably obtained using training data that includes text obtained from other messages between patients and therapists, and data relating to the characteristic.

The characteristic determined at the sixth step S106 may relate to a level of a psychological condition of the patient, a change in a level of a psychological condition of the patient, and/or a predicted level or change in level of a psychological condition of the patient at the end of therapy. The psychological condition may correspond to depression and/or anxiety. As will be explained in more detail below, the level of the psychological condition of the patient may be determined based on questionnaire scores (e.g. PHQ-9 scores, GAD-7 scores).

The characteristic may relate to a likelihood of the patient engaging in risky behaviour, e.g. self-harm.

The characteristic may relate to a likelihood of the patient (not engaging with and/or) dropping out of the therapy.

Preferably, the characteristic can take one of two values or classifications. One of the two values or classifications preferably corresponds to a situation or scenario of concern, e.g. a patient not being predicted to recover or improve. Alternatively, the characteristic can take one of three or more values or be a numerical value, etc.

The server 4 may determine several characteristics and may use several models.

In some examples, the server 4 determines one or more characteristics from the features obtained at the third step S103 without using a model obtained using supervised machine learning. This is suitable where characteristics can be directly determined from features.

In particular, as explained above, at the third step S103, the server 4 may determine one or more values ('topic values') describing a level to which the text relates to a topic. At the sixth step S106, the server 4 may determine one or more characteristics that are functions of the one or more topic values. For example, a characteristic may take one of two or more values in dependence upon a topic value being above or below one or more thresholds. The thresholds may be predetermined in any suitable way.

For example, topics may relate to risky behaviour by the patient, and topic values above particular thresholds may correspond to patients being classified as at risk.

Topics may relate to aspects of a particular psychological therapy approach, e.g. a cognitive behavioural therapy model. A characteristic may relate to a level to which a therapist follows the approach. Topic values below particular thresholds may correspond to therapists being classified as not following the approach sufficiently closely.

The model or models used may depend upon e.g. a characteristic of the patient and/or therapist (e.g. language used).

At an optional seventh step S107, the server 4 takes an action. This may involve providing an alert to a therapist and/or supervisor in dependence upon the characteristic(s) determined at the sixth step S106. For example, an alert can be provided if the characteristic is determined to have a value that corresponds to a situation or scenario of concern. Alerts can be provided in any suitable way, e.g. by way of a message or a web interface provided by the server 4 to the therapist or supervisor. Alternatively or additionally, the server 4 may store the characteristics for later use.

At an optional eighth step S108, the server 4 updates the one or more models used at the sixth step S106. This involves obtaining data relating to the characteristic. This data may correspond to one or more scores determined from one or more questionnaires completed by the patient, as explained above in relation to the fifth step S105. The data relating to the characteristic, e.g. the one or more scores, are used, together with the text obtained at the first step S101 and optionally prepared at the second step S102, to make up training data to update the model.

The one or more models need not be updated in this way. For example, a model may be updated periodically or in response to events other than sessions, e.g. a patient dropping out of therapy. A model may be updated by a user, e.g. a supervisor. The server 4 may provide a web interface to enable a user to obtain an initial model or to update a model using data stored at the server 4 (messages between patients and therapists, data relating to a characteristic) as training data.

The topic model and/or set of frequently used words used in the third step S103 may also be updated in a similar manner.

First Example

Methods

Data

The data used in the first example consisted of the transcripts from 882 Cognitive Behavioural Therapy (CBT) treatment dialogues (sessions) between patients with depression and/or anxiety and their therapists using an online text-based chat system. The transcripts are from online CBT provided by Psychology Online, who deliver 'live' therapy from a qualified psychologist accessed via the internet (http://www.psychologyonline.co.uk). Of the 882 transcripts, 837 are between therapists and patients who were in an ongoing treatment program or had completed their treatment by the time the sample was collected. There are 167 patients in this sample (125 females and 42 males), with 35 different therapists (for 2 patients the identity of the therapist is unknown). The number of transcripts per patient ranges from 1 to 14, with a mean of 5.0 (standard deviation (s.d.) 2.7). For all of the measures based on the transcripts, as outlined below, all text typed by both the therapist and the patient was included. In addition to the transcripts themselves, each patient normally filled out two questionnaires prior to each session with their therapist. These are described below.

Outcomes

—Patient Health Questionnaire (PHQ-9)—

This is a self-administered diagnostic instrument for common mental disorders (see K. Kroenke and R. L. Spitzer. 2002. The PHQ-9: a new depression diagnostic and severity measure. *Psychiatr Ann,* 32(9):1-7). The PHQ-9 is the depression module, which scores each of the 9 DSM-IV criteria as '0' (not at all) to '3' (nearly every day). A higher score indicates higher levels of depression, with scores ranging from 0 to 27. It has been validated for use (see A. Martin et al. 2006. Validity of the brief patient health questionnaire mood scale (PHQ-9) in the general population. *General hospital psychiatry,* 28(1):71-77).

—Generalised Anxiety Disorder Scale (GAD-7)—

Similarly, the GAD-7 (see R. L. Spitzer et al. 2006. A brief measure for assessing generalized anxiety disorder: the GAD-7. *Archives of internal medicine,* 166(10):1092-1097) is a brief self-report scale of generalised anxiety disorder. This is a 7-item scale which scores each of the items as '0' (not at all) to '3' (nearly every day). A higher score indicates higher levels of anxiety.

—Outcome Measures—

For the data in the sample, PHQ-9 and GAD-7 were highly correlated ($r=0.811$, $p<0.001$) so for the results reported below PHQ-9 is focused on. As each patient filled in the PHQ-9 before each consultation, two different outcome measures were used: PHQ now—the PHQ-9 score of the patient for the questionnaire completed immediately prior to the consultation; and PHQ start-now—the difference between the PHQ-9 score prior to any treatment and PHQ now, i.e. a measure of progress (how much better or worse the patient is since the start of their treatment). Although these two measures are numerical, one of the general aims of the research is to identify patients at risk. The outcome measures were therefore binarised and the task treated as a categorisation problem to identify the group of interest. For PHQ now, these were patients with moderate to severe symptoms; for PHQ start-now, patients whose PHQ score had not improved.

Topics

The transcripts from the 882 treatment consultations were analysed using an unsupervised probabilistic topic model, using MALLET (see A. K. McCallum. 2002. MALLET: A machine learning for language toolkit. http://mallet.cs.umass.edu.) to apply standard Latent Dirichlet Allocation (see D. Blei et al. 2003. Latent Dirichlet allocation. *Journal of Machine Learning Research,* 3:993-1022), with the notion of document corresponding to a single consultation session, represented as the sequence of words typed by any speaker. Stop words (common words which do not contribute to the content, e.g. 'the', 'to') were removed as usual, but the word list had to be augmented for text chat conventions and spellings (e.g. unpunctuated 'ive'). Additionally, common mispellings were mapped to their correctly spelled equivalents using a Microsoft® Excel® inbuilt spellchecker. This was due to the nature of text chat, in contrast to transcribed speech or formal text—the word 'questionnaire', for example, was found to have been typed in 21 different ways. The number of topics was set to 20, the default setting of 1000 Gibbs sampling iterations used, and automatic hyperparameter optimisation enabled to allow an uneven distribution of topics via an asymmetric prior over the document-topic distributions (see H. M. Wallach et al. 2009. Rethinking LDA: Why priors matter. In *NIPS,* volume 22, pages 1973-1981).

As in face-to-face therapy, it was found most topics were composed of coherent word lists, with many corresponding to common themes in therapy e.g. family (Topic 12), symptoms (16), treatment process (2, 14), and issues in work and social life (19, 5)—see Table 5.

Sentiment and Emotion Analysis

Each turn in the transcripts was then annotated for strength of positive and negative sentiment, and level of anger. Three approaches were compared: the dictionary-based LIWC (see J. W. Pennebaker et al. Linguistic inquiry and word count (LIWC): A computerized text analysis program. Austin, Tex.: LIWC.net) and two machine learning approaches, the Stanford classifier based on deep neural nets and parse structure trained on standard text (see R. Socher et al. 2013. Recursive deep models for semantic compositionality over a sentiment treebank. In *Proceedings of the 2013 Conference on Empirical Methods in Natural Language Processing,* pages 1631-1642), and one based on distant supervision over social media text, Sentimental (see M. Purver and S. Battersby. 2012. Experimenting with distant supervision for emotion classification. In *Proceedings of the 13th Conference of the European Chapter of the Association for Computational Linguistics (EACL),* pages 482-491). These are available from liwc.net, nlp.stanford.edu and Chatterbox Labs Ltd (London) respectively. None are specifically designed for therapy dialogue data; however, given the unorthodox spelling and vocabulary used in text chat, machine-learning based approaches, and training on "noisy" social media text, are expected to provide more robustness.

Each was used to provide a positive/negative/neutral sentiment value; for LIWC, this was taken from the relative magnitudes of the posemo and negemo categories. Two human judges then rated the 85 utterances in one transcript independently. Inter-annotator agreement was good, with Cohen's kappa=0.66. Agreement with LIWC was poor (0.43-0.45); with Stanford better (0.51-0.54); but best with Sentimental (0.63-0.80). For anger, LIWC gave only one utterance a non-zero rating, while Sentimental provided a range of values. Sentimental was therefore used in the experiments. Raw values per turn were scaled to $[-1,+1]$ for sentiment ($-1$ representing strong negative sentiment, $+1$ strong positive), and $[0,1]$ for anger; minimum, maximum, mean and standard deviation values per transcript were then derived.

Classification Experiments

A series of experiments was performed, to investigate whether various features of the transcripts could enable automatic detection of patient responses to the PHQ-9. The full range of possible features were calculated for each transcript—see Table 1. As well as topic, sentiment and emotion features as detailed above, raw lexical features are included to characterise details of content, and some high-level features (amount of talk; patient demographics; and therapist identity, known to affect outcomes).

TABLE 1

Feature sets for classification experiments

| Feature set | Description |
|---|---|
| AgentID | Identity of the therapist |
| High level (H/L) | Client gender; client age group; session number; client/agent number of words and turns used; proportion of all words per participant |
| Topic | Probability distribution of topics per transcript (one value per topic per transcript) |
| Sentiment | Overall sentiment mean, standard deviation, minimum and maximum; overall anger mean, standard deviation, minimum and maximum |
| Word | Unigrams, for all words that appeared in at least 20 of the transcripts, regardless of speaker; the features were the normalised counts of each word |
| N-gram | As word, but including unigrams, bigrams and trigrams |

In each case, the Weka machine learning toolkit (see M. Hall et al. 2009. The WEKA data mining software: An update. *SIGDKDD Explorations*, 11(1):10-18) was used to pre-process data, and a decision tree classifier (J48), a logistic regression model and the support vector machine implementation LibLINEAR (C.-C. Chang and C.-J. Lin, 2001. *LIBSVM: a library for Support Vector Machines*. Software available at http://www.csie.ntu.edu.tw/~cjlin/liblinear/) were used as classifiers. PHQ now was binarised based on the classification in Kroenke and Spitzer (cited above), whereby scores of 10 or over are moderate to severe (in-caseness) and scores of less than 10 are mild (out-of-caseness). PHQ start-now was binarised according to whether there was an improvement (reduction) in the PHQ score or not. Positive scores indicate an improvement; scores of 0 or lower indicate no change or a worsening of PHQ score. Each outcome indicator was tested with different feature sets using 10-fold cross-validation (The data are partitioned into 10 equal subsamples, and use each subsample as the test data for a model trained on the remaining 90%. This is repeated for each subsample (the 10 folds), and the test predictions collated to give the overall results. This partitioning is done by transcript: different transcripts from the same patient may therefore appear in training and test data within the same fold; the use of low-dimensional topic/sentiment features should minimise over-fitting).

Results
Correlations

First, statistical associations between the outcome measures and the available features (see above) were examined. R-values are shown for all significant correlations (at the p<0.05 level) in Tables 2 to 4. For the PHQ now measure, a positive correlation means a greater value of the feature is associated with a greater value of the PHQ score (i.e. a higher level of symptoms). For the PHQ start-now measures, a positive correlation means that a greater value of the feature is associated with a greater improvement in the PHQ score since the start of treatment. Correlations greater than ±0.2 are shown in bold.

—High-Level—

With patients with a worse (higher) PHQ score (PHQ now), more words and turns are typed by both participants. Better overall progress scores are also weakly associated with the amount of talk, with fewer turns typed by both participants if patients' PHQ score has improved by a greater amount since the start of their treatment program (see Table 2).

TABLE 2

Significant correlations of high-level features and outcomes

| Measure | PHQ now | PHQ start-now |
|---|---|---|
| Agent number of words | 0.231 | |
| Client number of words | 0.195 | |
| Agent number of turns | 0.149 | −0.080 |
| Client number of turns | 0.193 | 0.071 |

—Sentiment—

As shown in Table 3, more negative sentiment expressed in the transcripts (mean and minimum), a higher variability of sentiment between negative and positive (s.d.), and greater levels of anger (mean and maximum) are associated with worse PHQ scores. More positive sentiments (mean and maximum) are also associated with better progress.

TABLE 3

Significant correlations of sentiment features and outcomes

| Measure | PHQ now | PHQ start-now |
|---|---|---|
| Sentiment mean | −0.237 | 0.119 |
| Sentiment s.d. | 0.161 | |
| Sentiment minimum | −0.167 | |
| Sentiment maximum | | 0.074 |
| Anger mean | 0.185 | |
| Anger s.d. | 0.074 | |
| Anger minimum | | |
| Anger maximum | 0.192 | |

—Topic—

Topics 2, 6, 9, 10, 16 and 17 are negatively correlated with PHQ scores, i.e. higher levels of these topics are associated with better PHQ (see Table 4). Some of these topics involve words related to assessing the patient's progress and feedback, e.g. topic 2 includes session, goals and questionnaires, and topic 17 includes good, work and positive. Others relate to specific concerns of the patient, e.g. topic 6 (worry, worrying and problem) and topic 16 (anxiety, fear and sick). The top twenty words assigned to each topic by LDA, and the direction of significant correlations are shown in Table 5.

TABLE 4

Significant correlations of topic features and outcomes

| Measure | PHQ now | PHQ start-now |
|---|---|---|
| Topic 2 | −0.157 | 0.112 |
| Topic 4 | 0.124 | |
| Topic 5 | 0.176 | |
| Topic 6 | −0.117 | |
| Topic 7 | 0.217 | |
| Topic 8 | 0.093 | −0.126 |
| Topic 9 | −0.077 | |
| Topic 10 | −0.149 | |
| Topic 11 | 0.140 | |
| Topic 12 | 0.080 | |
| Topic 15 | 0.072 | |
| Topic 16 | −0.112 | |
| Topic 17 | −0.211 | 0.079 |
| Topic 18 | 0.121 | |

TABLE 5

Top 20 words per topic; correlations between topic and outcome and sentiment features ('+' denotes positive correlation, '−' negative correlation).

| Topic | PHQ now | Sentiment | Anger | Keywords |
|---|---|---|---|---|
| 0 | | − | + | good thought re well also mindfulness hw thoughts now vc maybe prob message neg just wk one self bit |
| 1 | | | | people good others self evidence thought enough wrong negative esteem thinking say confidence beliefs person true someone belief situation |
| 2 | − | + | − | session send goals next week last sent read great think questionnaires also homework goal appointment set time cbt able |
| 3 | | + | | thoughts thinking unhelpful helpful look thought behaviours go feelings may think anxiety negative try aware behaviour agenda start self |
| 4 | + | − | | feel think like just good really week now know last session next say felt people thoughts going feeling bit |
| 5 | + | − | + | sleep bed day week work get night mood time diary see better much sleeping activity house routine done activities |
| 6 | − | | | worry worrying worries bit stop train worried problem go example idea control hierarchy driving exposure home happen worst car |
| 7 | + | − | | help feel gp depression thank understand therapy now feeling life today think problems able little message medication sorry make |
| 8 | + | | | check checking ocd thoughts anxiety try something difficult danger brain week sense threat helpful away rituals anxious elephant images |
| 9 | − | | − | think time like much way sure see though know look lot sounds well also right thing sorry sense different |
| 10 | − | + | | thought thoughts anxiety really situation situations one week next example social experience record great emotions thanks notice see make |
| 11 | + | | + | things get time go need like want now just something feel know one work good day going give next |
| 12 | + | − | + | mum relationship husband life family dad parents never love feelings children said years mother much hard way told sister |
| 13 | | | | really week think appointment homework however lets teeth questions great just ready start may dentist set end sure therapy |
| 14 | | + | − | great right sure appointment just thank well tonight loo lol good say really cool get going sorry transcript absolutely |
| 15 | | + | − | things like get bit good sounds feeling also something really great today think idea send week useful anything make |
| 16 | − | | − | anxiety panic breathing get anxious feeling going go attack fear physical control try happen sick symptoms times cope distraction |
| 17 | − | + | − | good work well positive back help really time still last much weeks use thanks session better keep done things |
| 18 | + | | | eating eat food weight day week meal lunch dinner pie energy good mum put table public walk believe ate |
| 19 | | + | + | work job anger angry school stress thanks wife team stuff issues also boss year assertiveness assertive meeting kids times |

Conversely, topics 4, 5, 7, 8, 11 and 18 are positively correlated with PHQ scores, meaning more talk assigned to these topics is associated with worse PHQ. Several of these topics relate to specific issues, such as topic 5 (sleep, bed, night) and topic 18 (eating, food, weight). Some of these topics display overlap with the previous group (e.g. topics 2 and 4 both contain words reviewing progress such as session, week, next and last); this suggests that some topics (e.g. progress or particular issues) are discussed in importantly (and recognisably) different ways or contexts (possibly different emotional valences—see below), and these differences are being identified by the automatic topic modelling.

Similarly, greater amounts of talk in topics 2, 15 and 17 are weakly associated with better progress. These are the topics identified above as involving words related to assessing progress, and feedback. Greater amounts of talk in topic 8 (checking, OCD, anxiety, rituals) is associated with worse progress.

—Cross-Correlations Between Topic and Sentiment Features—

Previous work has hypothesised that automatically derived topics may differ from hand-coded topics in picking up additional factors of the communication such as valence. To explore this on a global level (i.e. at the level of the transcript, rather than at the finer-grained level of the turn) cross-correlations between sentiment and topic were examined. This initial exploration offers support for this hypothesis, as can be seen in Table 6. For example, topics 3 and 4 both contain words relating to feelings and thoughts, but topic 3 is positively correlated with sentiment, while topic 4 is negatively correlated. These correlations indicate a complex relationship between topic and sentiment; a joint topic-sentiment model might be appropriate. Although some topics pattern consistently with sentiment (e.g. topic 12, with words about relatives and relationships, is associated with negative sentiments and higher levels of anger) some do not (e.g. topic 19 is associated with more positive sentiment, but greater anger). Examination suggests that this topic involves discussions about feelings of anger, but not necessarily expressing anger, and also may include talk on how to deal with such feelings (with words like assertive). These observations may indicate that in this domain, in which people explicitly talk about their feelings, fully accurate sentiment and emotion analysis may require a different approach than in domains such as social media analysis.

TABLE 6

Significant correlations between topic and sentiment features

| | Sentiment | | | | Anger | | | |
|---|---|---|---|---|---|---|---|---|
| Measure | mean | s.d. | min | max | mean | s.d. | min | max |
| Topic 0 | −0.083 | 0.189 | −0.234 | 0.206 | 0.329 | 0.343 | −0.144 | 0.267 |
| Topic 1 | 0.087 | 0.083 | | | | | | |
| Topic 2 | 0.245 | −0.180 | 0.202 | −0.135 | −0.175 | −0.109 | 0.076 | −0.176 |
| Topic 3 | 0.113 | −0.213 | 0.159 | −0.135 | −0.123 | 0.110 | 0.095 | |
| Topic 4 | −0.350 | 0.324 | −0.201 | 0.099 | 0.074 | | | |
| Topic 5 | −0.079 | 0.119 | | | | | | |
| Topic 6 | 0.068 | | | | | | | |
| Topic 7 | −0.083 | −0.167 | −0.109 | 0.110 | | | | |
| Topic 8 | 0.078 | 0.123 | −0.104 | | | | | |
| Topic 9 | −0.072 | −0.071 | −0.075 | | | | | |
| Topic 10 | 0.100 | −0.167 | 0.133 | −0.073 | | | | |
| Topic 11 | 0.086 | 0.161 | 0.132 | 0.121 | | | | |
| Topic 12 | −0.338 | 0.182 | −0.156 | 0.233 | 0.092 | −0.087 | 0.146 | |
| Topic 13 | −0.111 | −0.112 | −0.243 | 0.077 | −0.089 | | | |
| Topic 14 | 0.112 | 0.156 | −0.183 | 0.186 | −0.087 | 0.225 | −0.116 | 0.204 |
| Topic 15 | 0.140 | −0.179 | 0.072 | −0.064 | −0.161 | −0.156 | −0.070 | |
| Topic 16 | −0.090 | −0.089 | 0.073 | −0.115 | | | | |
| Topic 17 | 0.385 | −0.156 | 0.267 | −0.116 | −0.408 | −0.139 | 0.078 | −0.288 |
| Topic 18 | −0.071 | | | | | | | |
| Topic 19 | 0.177 | 0.209 | | | | | | |

Classification Experiments

Results of classification experiments on different feature sets are shown in Tables 7 to 9. For each experiment, the weighted average f-score is shown, with the f-score for the class of interest shown in brackets. For PHQ now the class of interest is patients with high (moderate to severe) PHQ-9 scores; for PHQ start-now, the class of interest is patients who are not getting better. As a baseline, the proportion of the data in the class of interest in each case is shown in the first column in Table 7—note that these are not exactly 50%, but reflect the actual proportions in the data.

—High-Level—

As can be seen in Table 7, if a feature set consisting of high-level features and AgentID is used, PHQ now and PHQ start-now can be predicted reasonably well (>0.7). However, given the nature of the data, it is uncommon for a therapist to have many clients of the same age group and gender; these features can therefore act as a reasonable proxy for identifying individual patients, meaning that this result is somewhat spurious. Also, although identity of therapist is an important factor in therapeutic outcomes, one would like to identify aspects of the communication that explain why particular therapists are more successful than others, and generalise the findings to new therapists. AgentID was therefore removed in all subsequent experiments.

TABLE 7

Weighted average f-scores of outcomes using different high-level feature groups (figures in brackets are the f-scores for the class of interest; i.e. PHQ now - patients with higher/more symptomatic PHQ; PHQ start-now - patients showing no change or a worsening in PHQ)

| | | | High-Level (H/L), J48 | |
|---|---|---|---|---|
| Measure | Baseline Proportion | AgentID only, OneR | including AgentID | excluding AgentID |
| PHQ now | 40.5% | 0.584 (0.360) | 0.738 (0.637) | 0.640 (0.561) |
| PHQ start-now | 38.1% | 0.639 (0.446) | 0.707 (0.611) | 0.545 (0.299) |

—Sentiment and Topic—

As shown in Table 8, using the proportions of derived topics by transcript as features does allow prediction of whether a patient has a high PHQ now score reasonably well; but sentiment alone performs poorly. Combining sentiment and topic features, however, allows prediction of PHQ now with scores of around 0.7 (i.e. approaching the accuracy achieved using high level and AgentID features above). Prediction of the progress measure is less effective.

TABLE 8

Weighted average f-scores using sentiment/topic features (figures in brackets are the f-scores for the class of interest)

| | | Sentiment | | Topic | | Sentiment + Topic | |
|---|---|---|---|---|---|---|---|
| | Measure | including H/L | excluding H/L | including H/L | excluding H/L | including H/L | excluding H/L |
| J48 | PHQ now | 0.625 (0.528) | 0.610 (0.437) | 0.642 (0.548) | 0.650 (0.512) | 0.641 (0.544) | 0.638 (0.522) |
| | PHQ start-now | 0.630 (0.412) | 0.508 (0.094) | 0.628 (0.479) | 0.477 (0.024) | 0.619 (0.474) | 0.526 (0.147) |
| Logistic Regr. | PHQ now | 0.626 (0.497) | 0.610 (0.432) | 0.689 (0.585) | 0.658 (0.537) | 0.707 (0.613) | 0.674 (0.559) |
| | PHQ start-now | 0.532 (0.218) | 0.605 (0.025) | 0.593 (0.369) | 0.569 (0.283) | 0.591 (0.377) | 0.557 (0.295) |

—Words and n-Grams—

For the symptom measure, using words and n-grams gives f-scores (see Table 9) in line with those using only the reduced dimensionality of sentiment and topic. This is surprising; one might expect finer-grained lexical features (which provide more information via a much higher-dimensional feature space) to increase predictivity; on the other hand, it is also promising as it suggests that meaningful generalisations can be drawn out of this data using natural language processing techniques.

For the progress measure, on the other hand, n-gram features perform better than topic/sentiment (though not as well as on the symptom measures); this suggests that there are aspects of the communication that can assist in predicting patient progress, but that they are not fully captured by the topic and sentiment information as currently defined. This suggests that dialogue structure or style may play a role; one possibility is to look at topic and/or sentiment at a finer-grained level and examine their dynamics (e.g. are positive sentiments expressed near the start or end of a consultation linked to better progress)?

TABLE 9

Weighted average f-scores using raw lexical features (words/n-grams) using LibLINEAR (figures in brackets are the f-scores for the class of interest)

| | Words | | N-grams | |
|---|---|---|---|---|
| Measure | including H/L | excluding H/L | including H/L | excluding H/L |
| PHQ now | 0.655 (0.575) | 0.676 (0.614) | 0.696 (0.615) | 0.686 (0.616) |
| PHQ start-now | 0.616 (0.528) | 0.623 (0.506) | 0.626 (0.459) | 0.645 (0.532) |

Discussion

Standard topic, sentiment and emotion modelling can be usefully applied to online text therapy dialogue, although care is needed choosing and applying a technique suitable for the idiosyncratic language and spelling. The resulting information allows prediction of aspects of symptom severity and patient progress with reasonable degrees of accuracy, without requiring knowledge of therapist identity. However, some measures of patient progress are predicted better with fine-grained, high-dimensional lexical features, suggesting that insight into style and/or dialogue structure may be desirable, beyond simple topic or sentiment analysis.

Second Example

Methods

The second example generally used the same methods as the first example.

The data used in the second example consisted of the transcripts from 2066 sessions. This data includes the data used in the first example. Of the 2066 transcripts, 1864 are between therapists and patients who were in an ongoing treatment program or had completed their treatment by the time the sample was collected. There are 500 patients in this sample (352 females, 146 males, 2 unknown), with 64 different therapists (for 2 patients the identity of the therapist is unknown). The number of transcripts per patient ranges from 1 to 15, with a mean of 5.65.

Results

Correlations

Correlation results for the second example are shown in Tables 10 to 12.

The topics determined in the second example are mostly coherent word lists, and can be manually qualitatively assessed and labelled. Some of the topics are similar to topics determined in the first example. The numbering of topics in the two examples is unrelated. Some topics are correlated with severity (PHQ now) and progress (PHQ start-now) as shown in Table 10.

TABLE 10

Correlations of topic features and outcomes ('−−' denotes strong negative correlation, '−' negative correlation, '+' positive correlation, '++' strong positive correlation).

| Topic | Label | PHQ now | PHQ start-now |
|---|---|---|---|
| 0 | Materials, self-help, procedures | − | |
| 1 | Feelings/effects of relationships on sense of self | + | + |
| 2 | Positive reactions/encouragement | | |
| 3 | Issues around food | | |
| 4 | Family/relationships & issues with (mostly negative) | + | |
| 5 | Responses to social situations | | |
| 6 | Breaking things down into steps | + | |
| 7 | Worries/fears/anxieties | − | |
| 8 | Managing negative thoughts/mindfulness | | |
| 9 | Fears, checking, rituals, phobias | − | − |
| 10 | Unhelpful thinking/habits | | |
| 11 | Work/training/education issues/goals | | |
| 12 | Agenda/goal setting & review | | |
| 13 | Panic attack description/explanation | − | − |
| 14 | Other healthcare professionals, crises, risk, interventions | ++ | |
| 15 | Sleep/daily routine | + | |
| 16 | Positive progress, improvements | − | − |
| 17 | Feelings, specific occasions/thoughts | | |
| 18 | Explaining/framing in terms of CBT Model | | + |
| 19 | Techniques for taking control | − | − |

As shown in Table 11, a more positive sentiment is correlated with lower severity (PHQ now) and better progress (PHQ start-now). More variable sentiment is correlated with worse progress. More or more variable anger is correlated with higher severity.

TABLE 11

Correlations of sentiment features and outcomes.

| Measure | PHQ now | PHQ start-now |
|---|---|---|
| Sentiment mean | − | − |
| Sentiment s.d. | | + |
| Anger mean/maximum | + | |
| Anger s.d. | + | |

Words and n-grams positively and negatively correlated with severity (PHQ now) are shown in Table 12.

TABLE 12

Correlations of word/n-gram features with outcome (PHQ now).

| | Positive correlations | Negative correlations |
|---|---|---|
| Words | progress future definitely scenario welcome might further outcomes good wonder great using hi recommend relapse excellent Probably wishes trust continued situations interesting | anyone opposite makes mood yeah dogs walks tablets difficult never worse tv check depression urge useless horrible ignore meds married sleeping pills |
| N-grams | our last great progress relapse definitely hi NAME our last session good the future I wonder welcome think it's I've I think hi in terms of further 've had a really well of anxiety it's last session | anyone urge to who you but you at the and feeling to check who walks idea is yeah sleeping I get said it worse ever makes the idea is check meds difficult get |

Classification Experiments

Tables 13 to 16 show the results of the classification experiments in the second example.

Table 13 is concerned with various features that can be described as coarse-grained features. Similarly to the first example, there is some classification accuracy for severity (PHQ now), but less for progress (PHQ start-now).

TABLE 13

Weighted average f-scores of outcomes using various features (figures in brackets are the f-scores for the class of interest). Not including the H/L features leads to a 1-3% reduction.

| Measure | Baseline Proportion | H/L only | H/L + Sentiment | H/L + Topic | H/L + Sentiment + Topic |
|---|---|---|---|---|---|
| PHQ now | 46.4% | 0.50 (0.47) | 0.60 (0.53) | 0.62 (0.58) | 0.63 (0.58) |
| PHQ start-now | 33.2% | 0.55 (0.16) | 0.58 (0.21) | 0.60 (0.28) | 0.60 (0.30) |

Table 14 is particularly concerned with the word/n-gram features, which can be described as fine-grained features. In contrast to the coarse-grained features, the fine-grained features allow prediction of progress and also final severity (PHQ final).

TABLE 14

Weighted average f-scores of outcomes using various features (figures in brackets are the f-scores for the class of interest).

| Measure | Baseline Proportion | H/L + Sentiment + Topic | H/L + Words | H/L + N-grams |
|---|---|---|---|---|
| PHQ now | 46.4% | 0.63 (0.58) | 0.60 (0.56) | 0.66 (0.62) |
| PHQ start-now | 33.2% | 0.60 (0.30) | 0.60 (0.37) | 0.61 (0.39) |
| PHQ final | 25.5% | 0.60 (0.06) | 0.61 (0.33) | 0.66 (0.34) |

Table 15 is concerned with the prediction of final outcomes, i.e. whether a patient is in- or out-of-caseness at the end of a course of treatment. In the column labelled 'features I', the features used in the model are H/L, Sentiment and Topic for the first treatment session; H/L, Sentiment and Topic for the final treatment session; and the change in Sentiment and Topic between the first and final treatment sessions. In the column labelled 'features II', the features used in the model are PHQ scores obtained at an assessment session and the subsequent first treatment session; and mean anger, topic 14 (other healthcare professionals, crises, risk, interventions) and topic 16 (positive progress, improvements) for the final treatment session. Final in-caseness can be predicted with greater than 70% accuracy for features I and greater than 75% accuracy for features II. The table also shows results for patients who were also in-caseness at the start of the course of treatment.

Final in-caseness should also be sufficiently accurately predictable using features for one or more earlier treatment sessions rather than the final treatment session.

TABLE 15

Weighted average f-scores of final outcomes using various features (figures in brackets are the f-scores for the class of interest -patients who are in-caseness at the end of a course of therapy).

| | Baseline Proportion | Features I | Features II |
|---|---|---|---|
| Final in-caseness | 26.8% | 0.71 (0.48) | 0.76 (0.51) |
| Start in-caseness and final in-caseness | 37.9% | 0.62 (0.49) | 0.65 (0.49) |

Table 16 is concerned with predicting non-engagement and drop-out, i.e. patients not entering or staying in therapy. This applied to 148 of the 500 patients. Results were obtained using text from the assessment session only, the first treatment session only and both sessions. For the assessment session only, the features used in the model were H/L, Sentiment and Topic. For the first treatment session only and both sessions, the features used in the model were H/L, Sentiment, Topic and Words. Dropout/non-engagement can be predicted with greater than 70% accuracy when features of both the assessment session and the first treatment session are used.

TABLE 16

Weighted average f-scores of dropout outcomes using various features (figures in brackets are the f-scores for the class of interest).

| | Baseline Proportion | Features for assessment session | Features for first treatment session | Features for both sessions |
|---|---|---|---|---|
| Dropout | 29.6% | 0.65 (0.26) | 0.70 (0.48) | 0.73 (0.52) |

Modifications

It will be appreciated that many other modifications may be made to the embodiments hereinbefore described.

For example, the therapy may be of a type other than cognitive behavioural therapy.

The method may be applied to text-based messages sent in other contexts and for other purposes.

The invention claimed is:

1. A computer-implemented method comprising:
   obtaining text from text-based messages sent via an instant messaging system between a patient and a therapist during a psychological therapy session;
   determining at least one feature of the text;
   determining a characteristic of the patient and/or the therapist using the at least one feature, wherein the characteristic relates to a predicted level or change in level of a psychological condition of the patient at the end of a course of therapy; and
   taking an action in dependence upon the determined characteristic, the action comprising providing an alert to the therapist and/or a supervisor.

2. A method according to claim 1, comprising determining the characteristic using the at least one feature and a model obtained using supervised machine learning.

3. A method according to claim 2, comprising obtaining the model using training data comprising text obtained from other messages between patients and therapists and data relating to the characteristic.

4. A method according to claim 1, wherein the at least one feature comprises at least one value describing a level to which the text relates to a topic.

5. A method according to claim 4, comprising determining one or more topics using a topic model and text obtained from other messages between patients and therapists.

6. A method according to claim 1, wherein the at least one feature comprises at least one value describing an emotional state.

7. A method according to claim 6, wherein the emotional state corresponds to positive/negative sentiment and/or anger.

8. A method according to claim 6, wherein the at least one value describing the emotional state describes a level or a variability of the emotional state.

9. A method according to claim 6, comprising determining the at least one value describing the emotional state using a model obtained using supervised machine learning.

10. A method according to claim 1, wherein the at least one feature comprises at least one value relating to a frequency of a word or sequence of words in the text.

11. A method according to claim 10, wherein each word or sequence of words is one of a set of most frequently-used words or sequences of words in text obtained from other messages between patients and therapists.

12. A method according to claim 1, comprising:
   obtaining at least one further feature including at least one feature of text obtained from text-based messages previously sent between the patient and therapist; and
   determining the characteristic using the at least one feature and the at least one further feature.

13. A method according to claim 1, comprising:
   obtaining data relating to the patient, the therapist and/or communications therebetween; and
   determining the characteristic using the at least one feature and the data.

14. A method according to claim 1, wherein obtaining the text comprises replacing words or sequences of words with alternatives, wherein each alternative can replace a plurality of different words or sequences of words.

15. A method according to claim 1, wherein the characteristic relates to a level of a psychological condition of the patient and/or a change in a level of a psychological condition of the patient.

16. A method according to claim 15, wherein the psychological condition corresponds to depression and/or anxiety and the level of the psychological condition of the patient is determined based on a Patient Health Questionnaire PHQ-9, a Generalized Anxiety Disorder Scale GAD-7, or a combination thereof.

17. A method according to claim 1, wherein the characteristic relates to a likelihood of the patient engaging in risky behaviour.

18. A method according to claim 1, wherein the characteristic relates to a level to which a therapist follows a particular psychological therapy approach.

19. A method according to claim 1, wherein the characteristic can take one of two values, one of the two values corresponding to a situation or scenario of concern.

20. A method according to claim 19, comprising using three or more features of the text to predict the situation or scenario of concern with an accuracy of greater than 70%.

21. A method according to claim 1, comprising obtaining the text from messages sent by more than one patient and/or by more than one therapist.

22. An apparatus configured to perform a method according to claim 1.

23. The apparatus according to claim 22, comprising:
   at least one processor; and
   at least one memory including computer program code;
   the at least one memory and the computer program code configured to, with the at least one processor, cause the apparatus to perform the method.

24. Computer program code comprising instructions for performing a method according to claim 1.

25. A computer-readable medium storing computer program code according to claim 24.

26. A computer-implemented method according to claim 1, further comprising an initial step of detecting that a session of therapy has completed and in response initiating the method according to claim 1.

27. A method according to claim 1, wherein the characteristic relates to dropping out of the therapy.

* * * * *